United States Patent [19]

Shaw

[11] Patent Number: 5,155,275
[45] Date of Patent: Oct. 13, 1992

[54] PREPARATION OF HIGH PURITY POLYSULFIDES

[75] Inventor: James E. Shaw, Bartlesville, Okla.

[73] Assignee: Phillips Petroleum Company, Bartlesville, Okla.

[21] Appl. No.: 718,693

[22] Filed: Aug. 21, 1991

[51] Int. Cl.$^5$ .............................................. C07C 321/14
[52] U.S. Cl. .......................................... 568/21; 568/26
[58] Field of Search ....................................... 568/21, 26

[56] References Cited

U.S. PATENT DOCUMENTS 3,022,351  2/1962  Mihm et al. ........................ 260/608
3,308,166  3/1967  Biensan et al. ..................... 260/608

OTHER PUBLICATIONS

Reid, E. E., *Organic Chemistry of Bivalent Sulfur*, Ch. 2. 1958.

*Primary Examiner*—Marianne M. Cintins
*Assistant Examiner*—John Peabody
*Attorney, Agent, or Firm*—Gary L. Haag

[57] ABSTRACT

This invention relates to a process for preparing polysulfide product generally containing an average of 3 to 6 sulfur atoms in high yield which degrades minimally over extended time periods. Minimal degradation is accomplished by a unique treatment process wherein chemical species, most notably unreacted mercaptans and catalysts which apparently promote degradation, are selectively removed from the polysulfide crude product.

21 Claims, No Drawings

PREPARATION OF HIGH PURITY POLYSULFIDES

BACKGROUND OF THE INVENTION

This invention relates to the preparation of high purity and highly stable polysulfides.

Organic polysulfides and particularly dialkyl polysulfides such as tetra- and penta-sulfides have been found useful for many purposes such as additives for elastomers, antioxidants for lubricating oils, intermediates for the production of organic chemicals, insecticides, germicides and as an additive to diesel fuels to improve the cetane number and ignition qualities of these fuels. These compounds have also been found useful in the compounding of extreme pressure lubricants and in the acceleration of rubber treating processes.

Methodologies are known in the art for the preparation of polysulfides by the reaction of elemental sulfur with mercaptans in the presence of a basic catalyst (European Patent 25 944) or a basic catalyst with an alcohol promotor (U.S. Pat. Nos. 3,308,166 and 3,022,351). However, problems associated with product degradation are frequently observed for polysulfide product containing 3 or greater sulfur atoms per polysulfide molecule. This degradation can cause the product appearance to change from a clear yellow or orange to a cloudy appearance and ultimately, precipitation will result. Furthermore, the presence of mercaptan and hydrogen sulfide in the polysulfide product causes a very undesirable odor which end users desire to have absent.

SUMMARY OF THE INVENTION

It is an object of this invention is to provide a method for producing a high purity polysulfide.

A further object is to provide a method for producing a polysulfide product which does not degrade with time.

Yet a further object of this invention is to provide a novel method of producing polysulfide product containing an average of 3 to 6 sulfur atoms per polysulfide molecule.

A still further object of this invention is to provide a novel method for producing a polysulfide product which does not possess the undesirable odor associated with mercaptans and hydrogen sulfide.

It is yet a further object of this invention to provide a stable polysulfide product.

In accordance with this invention, product from the reaction of mercaptan with sulfur in the presence of a basic catalyst is treated with a high pH wash to give a polysulfide product which is resistant to degradation.

DETAILED DESCRIPTION OF THE INVENTION

The preparation of the highly stable polysulfide product of this invention is a two step process. These two steps are (a) the reaction of mercaptan with elemental sulfur in the presence of a basic catalyst to form the polysulfide crude product and (b) treatment of this crude product to remove species which apparently promote long term polysulfide degradation. The first step in the process, that is the reaction of mercaptans with elemental sulfur in the presence of a basic catalyst to form a polysulfide product, is known in the art. However, the second step or the product treatment step enables an improvement on the prior art to be made.

Key attributes of the new process are the ability to produce a polysulfide product generally containing an average of 3 to 6 sulfur atoms in high yield which degrades minimally over extended time periods. Minimal degradation is accomplished by a unique treatment process wherein chemical species, most notably unreacted mercaptans and catalysts which apparently promote degradation, are selectively removed from the polysulfide crude product.

The crude polysulfide products are obtained by a reaction which can be depicted as follows:

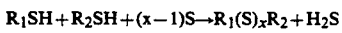

$$R_1SH + R_2SH + (x-1)S \rightarrow R_1(S)_xR_2 + H_2S$$

$R_1$ and $R_2$ are alkyl radicals, generally containing 1 to 20 carbon atoms, more preferably 3 to 15 carbon-atom tertiary alkyl radicals, and most preferably 9 to 12 carbon-atom tertiary alkyl radicals. In the preceeding equation, x is the average number of sulfur atoms per polysulfide molecule in the crude product. The invention is broadly applicable to any polysulfide product produced in the presence of a basic catalyst. Preferably, it is applicable to those having an average sulfur atom number per polysulfide molecule of 2 through 8, and most preferably to those having an average sulfur atom number per polysulfide molecule of 3 through 6.

The procedure to prepare crude polysulfide product consists generally of adding one of the reactants, either the mercaptan or sulfur, slowly to the other reactant in the presence of a basic catalyst. The order of reactant addition does not have a significant effect on the final product. However, the preferred method is to slowly add sulfur to the mercaptan/catalyst solution. The sulfur, upon addition, readily dissolves in the solution. Mixing of the solution and/or operating at greater than ambient temperatures will enhance the reaction rate. The amount of sulfur to be added is dependent on the desired sulfur content of the polysulfide product. For an average sulfur content of x-sulfurs per polysulfide molecule, $(x-1)$ moles of sulfur must be added and 1 mole of hydrogen sulfide will be released per 2 moles of mercaptan reacted. The catalyst should be basic in nature. Preferable catalyst include the primary, secondary, and tertiary alkyl and cycloaliphatic amines and the alkali metal and alkaline earth oxides and hydroxides. Most preferred are the tertiary alkylamines, particularly triethylamine. The weight of catalyst as a percentage of the weight of mercaptan should be 0.05 to 5%, preferably 0.1 to 2.0%, and most preferably 0.2 to 1.0%. Significant amounts of the reaction product, hydrogen sulfide, will be released as a gas during the reaction. Following completion of the reaction, residual hydrogen sulfide may be removed from the crude polysulfide product by either an inert gas purge or by vacuum stripping. When using an inert gas purge, preferably gases are nitrogen and air.

The second step in the preparation of highly stable polysulfides is the novel treatment process wherein a product which degrades minimally with time is obtained. This process apparently removes species from the crude product which promote long term polysulfide degradation. When present, this degradation may be observed by changes in the product color, the transparency/opacity of the product, and the presence of a precipitate. A key factor in the selection of this process methodology was the observation that small quantities of unreacted mercaptan and catalyst apparently have a detrimental affect on the long term appearance and stability of the polysulfide product. The following process was specifically tailored for the removal of these species.

Although not required, it is preferred that the crude product first be diluted with a volatile organic diluent. Preferably, this diluent is an aliphatic, aromatic or alkylaromatic containing 3 to 8 carbon atoms or mixtures thereof; more preferably it is an alkane containing 4 to 7 carbon atoms and most preferably, pentane. The dilution of the crude product apparently serves three important functions. First, because the crude product possesses a density similar to that of water and other desirable aqueous-based wash solutions, the addition of a less dense organic to the crude product decreases the density of the organic phase and thereby increases the density contrast between organic and aqueous phases. This in turn simplifies the separation of aqueous-based wash solutions from the organic. Second, because the volatile organic is significantly less viscous than the crude product, mixtures thereof will have a viscosity less than that of the crude product. This reduced organic phase viscosity enables better contacting of the organic with the aqueous wash solutions which in turn aids in the desired mass transfer of species which promote degradation from the organic to the aqueous phase. Finally, the choice of a diluent with a relatively high vapor pressure at near ambient conditions simplifies the final separation of the diluent from the purified polysulfide product.

To some degree, the operating conditions, particularly temperature and pressure, for the wash steps and separation of the diluent from the treated polysulfide product will be dependent on available process equipment, process economics, safety considerations and at the discretion of one skilled in the art. A major constraint regarding the wash steps is that the diluent remain in the liquid state. For a closed system, this can be accomplished by either increasing the system pressure above the bubble point pressure of the diluent or decreasing the system temperature such that the bubble point pressure of the diluent is below the system pressure. In contrast, a requirement of the diluent/purified product separation step is that the vapor pressure of the diluent be sufficient such that the diluent can be volatilized and removed. This can be accomplished by either increasing the diluent vapor pressure by increasing the system temperature or by operating at reduced pressures. As previously noted, the preferred temperature and pressure for a given diluent for the wash and separation steps can be established via the art and will be dependent on available process equipment, process economics, and safety considerations. The degree of crude product dilution by diluent is also dependent on various parameters which include available process equipment, process economics, and safety considerations and therefore at the discretion of one skilled in the art. The addition of any diluent to the crude product will aid in aqueous/organic contact during the wash steps and the subsequent phase separation. However, excessive amounts of diluent will make separation of the purified product from the diluent more difficult. A preferred range of crude product to diluent volume ratio is 0.25 to 4. A more preferred range is 1 to 3 volume parts crude product per volume part diluent. For the most preferred diluent, pentane, the most preferred ratio is approximately 2 volume parts crude product to 1 volume part pentane.

As previously noted, it has been experimentally observed that unreacted mercaptan and residual catalyst apparently promote polysulfide degradation. Studies have indicated that unreacted catalyst can be removed by contacting the organic polysulfide-bearing phase with a low pH aqueous phase. And in a similar manner, unreacted mercaptan can be removed by contacting the organic phase with a high pH aqueous phase. In general, the detrimental effects of residual catalyst appear to decrease as the carbon number of the mercaptan reactant increases. For t-dodecyl ($C_{12}$) mercaptan reactant, excellent results were obtained with just a high pH wash and no low pH wash. However for t-nonyl ($C_9$) mercaptan reactant, the low pH wash brought about a significant additional improvement over the high pH wash alone. In contrast, the difficulties associated with the removal of unreacted mercaptan by contacting with high pH aqueous solutions apparently increase with carbon number. Because mercaptan solubility in the wash fluid decreases with increasing carbon number, additional washes or greater volumes of a high pH wash fluid are required. These experimental observations are presented in greater detail in Examples I-IV.

If acid treatment and the associated removal of catalyst from the crude polysulfide product is desired to improve the stability of the polysulfide product, this is generally the first wash step. In preparing the low pH wash solution, preferably acids include but are not limited to, sulfuric, nitric, phosphoric, hydrochloric, hydrofluoric, and acetic. The preferred pH for the wash solution is 3 or less. A more preferred pH is 1.5 or less and a most preferred wash solution contains approximately 1 wt % sulfuric acid solution (possesses a pH of approximately 1). The volume ratio of organic to aqueous wash solution and the time and degree of contacting are dependent, at least to some extent, on the pH of the wash solution. Either batch or continuous means may be used for contacting the organic and aqueous phases. Means of contacting these phases include but are not limited to simple agitation by shaking the mixtures and the use of stirred tank reactors, mixer/settlers, Ruston reactors and packtowers with counterflow of organic and aqueous phases. For the preferred batch operation, 0.01 to 10 volume parts aqueous phase of pH 3 or less should be thoroughly contacted with 1 volume part organic for a nominal time period of 3 to 30 minutes. More preferably, 0.1 to 0.5 volume aqueous phase of pH 1.5 or less should be thoroughly contacted with 1 volume part organic for a nominal time period of 3 to 10 minutes. Most preferably, approximately 0.2 volume parts of approximately 1 wt % sulfuric acid should be thoroughly contacted for a nominal time period of 5 minutes per volume part organic. Following such contacting the phases are separated, preferably by simple decantation if the density differences are sufficient, and the less dense polysulfide-bearing organic phase recovered.

Improving the stability of the polysulfide by treatment with a basic solution, which among other things removes unreacted mercaptan, is accomplished by one or more washes of the polysulfide-bearing organic phase with a high pH aqueous phase. Though not inclusive, preferable bases include the alkali metal hydroxides, the alkaline earth hydroxides capable of pH 11 or greater, and ammonium hydroxide. The volume of aqueous phase and the contact time with organic phase is dependent on mercaptan solubility in the aqueous phase, the pH of the aqueous phase and the degree of mixing. The use of basic solutions for the extraction of mercaptans from organic solutions is established in the art. What is not established is the use of this technique for preparing a polysulfide product which degrades minimally with time.

Generally, the solubility of mercaptan in water decreases by 1 order of magnitude for every 2 additional carbon atoms on the alkyl chain. However, the solubility in the aqueous phase can be increased by at least 3 orders of magnitude by increasing the pH from 11 or less to a pH of 14. The pH of 14 corresponds to a 1.0N hydroxyl ion concentration. As an example, the solubility of nonylmercaptan is 0.00115 g/l in water and 2.3 g/l in 1.0N sodium hydroxide. For comparison purposes, the solubility of heptyl mercaptan which contains 2 less carbon atoms than nonyl mercaptan is an order of magnitude greater or 0.0138 g/l in water and 27.6 g/l in 1.0N sodium hydroxide. Additional increases in the solubility of mercaptan in the aqueous phase is possible by the addition of a solubilizer such as the lower carbon number alcohols, specifically methanol and ethanol. The use of solubilizers to increase mercaptan solubility in alkaline solutions is established in the art; again the uniqueness of this approach being the use of an alkaline wash to treat a polysulfide-bearing organic.

To successfully wash the polysulfide-bearing organic with a basic aqueous solution, sufficient aqueous phase must be present to ensure complete solubility of the mercaptan and the degree of mixing and contact time must be sufficient to ensure transfer of the mercaptan from the organic to the aqueous phase. As in the case of the previously discussed acid wash, this step can be performed in either a batch or a continuous mode. Means of contacting the organic and aqueous phases include but are not limited to agitation by shaking and the use of stirred tank reactors, mixer/settlers, Ruston reactors and pack towers with counterflow of aqueous and organic phases. In the preferred batch mode, the wash can consist of either a single or multiple contacting of the polysulfide-bearing product with the aqueous wash solution. After each wash, the phases are separated and the polysulfide-bearing organic phase recovered for additional treatment. Preferably, the capacity of the aqueous phase for mercaptan should be at least 10 times greater than the quantity of mercaptan present in the organic phase, the volume ratio of the aqueous to organic phase should be 0.2 to 1, phase contacting should be sufficient to ensure significant mercaptan transfer in less than one hour, and 3 or fewer washes required. Most preferably for the treatment of di-t-nonyl polysulfide-bearing organic, the organic is vigorously contacted with approximately 10 wt % sodium hydroxide in a volume ratio of approximately 0.20 volume parts aqueous phase per 1 volume part organic phase for approximately 5 minutes. (As a point of reference, 10 wt % sodium hydroxide is approximately equivalent to a 1N solution of sodium hydroxide and possesses a pH of approximately 14.) The phases are then separated and the organic phase recovered. Most preferably for the treatment of di-t-dodecyl polysulfide-bearing organic, the organic is first vigorously contacted with approximately 10 wt % sodium hydroxide solution in a volume ratio of 0.2 parts aqueous phase per volume part organic for approximately 5 minutes. Following recovery of the organic phase, the organic phase is then vigorously contacted with an approximate 5 wt % sodium hydroxide solution in a volume ratio of 0.2 volume parts of aqueous phase per volume parts organic for approximately 5 minutes. The phases are allowed to separate and the polysulfide-bearing organic phase recovered.

As previously noted when high and low pH washes are desired, the wash order can be interchanged. However, the preferred order is to conduct the low pH wash first.

As an optional polishing step, the polysulfide-bearing organic can be treated with a final water wash (i.e., a pH of approximately 7). Such a wash provides additional assurance that potentially undesirable water soluble components in the organic phase have been removed. Preferably, the organic is vigorously contacted with water at a volume ratio of 0.2 parts water per 1 part organic for approximately 5 minutes. The polysulfide-bearing organic phase is then recovered.

When using the preferred mode for treatment of the crude polysulfide product wherein the product has been diluted with a volatile organic, the final treatment step consists of the separation of treated polysulfide product from the volatile organic. Because the vapor pressure of the volatile organic is significantly greater than that of the polysulfide product, this separation is conducted at a temperature and pressure where significant quantities of the volatile organic can be vaporized. Because of concern with possible thermal degradation of the polysulfide product at higher temperatures, the process temperature is frequently reduced by conducting the vaporization at subatmospheric pressures. In the preferred mode, the organic is heated to approximately the boiling temperature of the volatile organic at atmospheric pressure and the system pressure maintained at subatmospheric conditions until solvent vaporization ceases. In another preferred mode, the organic is heated to near its boiling point and the volatiles are stripped by an inert gas purge until negligible organic is present in the inert gas. In the most preferred mode, when pentane is used as a diluent, the organic is heated to approximately the boiling point of pentane or 36° C. and at a pressure of less than 1 atmosphere until pentane evolution becomes minimal. To ensure complete pentane removal the remaining pot liquid is then maintained at 36° C. and is vacuumed stripped at a pressure of less than 100 torr for approximately 2 hours or more.

The following examples are provided to illustrate the practice of the invention and are not intended to limit the scope of the invention or the appended claims in any way.

EXAMPLE I

The preparation of di-t-nonyl polysulfide with an average of 5 sulfurs is performed in the following manner. To a 2 liter, 3 neck flask equipped with condenser, thermowell, and magnetic stirrer was added 721 grams (4.5 moles) t-nonyl mercaptan and 4.5 grams (0.044 mole) triethylamine. The solution was heated to 45° C. and 289 grams (9.0 mole). Sulfur (sublimed or flower of sulfur) was then added in small portions over 45 minutes at 45° C. Hydrogen sulfide was evolved during this addition. The solution was then heated with stirring at 45° C. for an additional 2.5 hours. A gas dispersion tube was then put in the solution and nitrogen gas was bubbled through the solution (approximately flourate of 2 scf/h) with stirring for a period of 4 hours at 45° C. The crude product was orange in color but turned cloudy within a day or two and large amounts of precipitate were present within a week.

After cooling, the liquid was transferred to a separatory funnel where 400 ml of n-pentane and 300 ml of aqueous 1% sulfuric acid solution were added. After shaking for approximately 3 minutes the phases were allowed to separate. The bottom aqueous phase was discarded and the top organic phase was washed with 300 grams of aqueous 10 wt % sodium hydroxide solution. After shaking for approximately 5 minutes, the phases were again allowed to separate. The bottom aqueous phase was discarded and the top organic phase was washed with 300 ml of water. The bottom layer was again discarded. The top organic layer was evaporated at a reduced pressure of approximately 20 torr and a temperature 45° C. or less. The purpose of this step was to remove most of the pentane. The remaining pot liquid was vacuum stripped by stirring at a pressure of 5 torr and a temperature of 45° C. for 2 hours. After cooling, the pot liquid was filtered and 928 grams of a clear yellow liquid product was obtained. This corresponds to a 99.4% yield based on 5 sulfur atoms per polysulfide molecule. The product maintained its clear yellow appearance with zero to minimal precipitant over a 6 month storage period. Analysis of the product revealed no catalyst and less than 26 ppm by weight mercaptan sulfur.

EXAMPLE II

The same conditions were used as in Example I with the exception that the sulfuric acid wash was eliminated. The final product contained 18 ppm nitrogen which is attributed to the by residual amine catalyst and 8 to 24 ppm by weight of mercaptan sulfur. The initial product solution was a clear yellow fluid as in Example I. However after 2 to 3 weeks, a very small quantity of yellow precipitant was observed and the solution became slightly hazy after 1 to 2 months. The product was still of very good quality and was far, far better than the untreated product. The addition of either catalyst or mercaptan caused the product to turn cloudy within 24 hours.

EXAMPLE III

The same conditions were used as in Example II except an additional wash with either water or 5 wt % sodium hydroxide was performed. Although the nitrogen content was reduced to 8 ppm by weight, a factor of 2 less than reported in Example II, product stability was not changed appreciably.

EXAMPLE IV

The preparation of di-t-dodecyl polysulfide with an average of 5 sulfurs per polysulfide molecule was performed in the following manner. To a 5 liter, 3 neck flask equipped with condenser thermowell and magnetic stirrer was added 1822 grams (9.00 mole) t-dodecyl mercaptan and 9.0 grams (0.089 mole) triethyl amine. The solution was heated to approximately 45° C. and then 578 grams (18.0 mole) sulfur (sublimed or flowers of sulfur) was added in small proportions for a 45 minute time period at a system temperature of 45° C. Hydrogen sulfide was evolved during this addition. The system was then maintained at 45° C. for an additional 2.5 hours and stirred. A gas dispersion tube was then inserted into the solution and nitrogen gas was bubbled through the solution (approximately 2 standard cubic feet per hour) with stirring for a time period of 4 hours and at a temperature of 45° C. The crude product that was obtained was orange in color and would gradually turn cloudy with time.

After cooling the liquid, the liquid was transferred to a separatory funnel. Pentane, 800 ml, was then added to the solution as a diluent. The solution was contacted with 600 grams of an aqueous 10 wt % sodium hydroxide solution. After shaking vigorously for approximately 5 minutes, the phases were allowed to separate. The bottom aqueous phase was discarded and the top organic phase was washed with 600 grams of aqueous 5 wt % sodium hydroxide solution. After shaking for approximately 5 minutes the phases were allowed to separate. The bottom aqueous phase was discarded and the top organic phase was washed with 400 ml of water. The bottom aqueous phase was again discarded and the top organic phase was evaporated under reduced pressure (approximately 20 torr) at 45° C. or less so as to remove most of the pentane. The remaining pot liquid was vacuum stripped with stirring at a pressure of approximately 5 torr and a temperature of 45° C. for approximately 2 hours. After cooling, the pot liquid was filtered and a clear yellow liquid was obtained. This product displayed excellent long term stability. The total mass of the product obtained was 2232 grams of polysulfide. Based on the average of 5 sulfur atoms per polysulfide molecule, this corresponds to a yield of 99.3%.

While this invention has been described in detail for the purpose of illustration, it is not to be construed or limited thereby but is intended to cover all changes and modifications within the scope and spirit thereof.

That which is claimed is:

1. A process for treating a crude polysulfide comprising the steps of:
   a) contacting said crude polysulfide with a high pH aqueous phase to produce a polysulfide-contacted high pH aqueous phase and a high pH treated polysulfide-bearing organic phase; and
   b) separating said polysulfide-contacted high pH aqueous phase and said high pH treated polysulfide-bearing organic phase, further comprising the following steps which are performed before the steps (a) and (b):
   c) contacting said crude polysulfide with a low pH aqueous phase to give a polysulfide-contacted low pH aqueous phase and a low pH treated polysulfide-bearing organic phase;
   d) separating said polysulfide-contacted low pH aqueous phase and said low pH treated polysulfide-bearing organic phase; and
   e) substituting said low pH treated polysulfide-bearing organic phase for said crude polysulfide in step (a).

2. A process according to claim 1 wherein said low pH aqueous phase has a pH of 3 or less and is prepared from an acid selected from the group consisting of: sulfuric, hydrochloric, nitric, phosphoric, acetic and mixtures thereof.

3. A process according to claim 1 further comprising:
   (f) diluting said crude polysulfide with a volatile organic compound prior to contacting with said low pH aqueous phase; and
   (g) drying said high pH treated polysulfide-bearing organic phase.

4. A process according to claim 3 wherein said high pH treated polysulfide-bearing organic phase is dried via vacuum stripping.

5. A process according to claim 3 wherein said high pH treated polysulfide-bearing organic phase is dried via an inert gas purge.

6. A process according to claim 3 wherein said high pH treated polysulfide-bearing organic phase is dried via heating.

7. A process according to claim 3 wherein said volatile organic compound is a $C_3$-$C_{10}$ hydrocarbon.

8. A process according to claim 3 wherein said volatile organic compound is pentane.

9. A process according to claim 3 further comprising:
(h) washing said high pH treated polysulfide-bearing organic phase with a neutral pH aqueous phase prior to said drying step of (g) to produce a polysulfide-contacted neutral aqueous phase and a neutral pH treated polysulfide-bearing organic phase; and
(i) separating said polysulfide-contacted neutral pH aqueous phase and said neutral pH treated polysulfide-bearing organic phase which is then passed to said drying step of (g).

10. A process according to claim 9 wherein said neutral pH treated polysulfide-bearing phase is filtered to remove solids.

11. A process according to claim 1 wherein said crude polysulfide is obtained by contacting elemental sulfur with alkyl mercaptans containing 3 to 20 carbon atoms in the presence of a basic catalyst.

12. A process according to claim 3 wherein said crude polysulfide is obtained by contacting elemental sulfur with alkyl mercaptans containing 3 to 20 carbons in the presence of a basic catalyst.

13. A process according to claim 9, wherein said crude polysulfide is obtained by contacting elemental sulfur with alkyl mercaptans containing 3 to 20 carbons in the presence of a basic catalyst.

14. A process according to claim 10 wherein said crude polysulfide is obtained by contacting elemental sulfur with alkyl mercaptans containing 3 to 20 carbons in the presence of a basic catalyst.

15. A process for treating a crude di-t-nonyl polysulfide prepared from monomer containing an average of 3 through 6 sulfur atoms per monomer unit comprising the steps of:
(a) diluting said crude di-t-nonyl polysulfide with pentane to form a polysulfide-bearing organic phase;
(b) contacting said polysulfide-bearing organic phase with an aqueous phase containing sulfuric acid which possesses a pH of 3 or less;
(c) separating the aqueous and organic phases resulting from step (b);
(d) contacting the polysulfide-bearing organic phase resulting from step (c) with a sodium hydroxide aqueous phase which possesses a pH of 11 or greater;
(e) separating the aqueous and organic phases resulting from step (d);
(f) contacting the polysulfide-bearing organic phase resulting from step (e) with water;
(g) separating the organic and aqueous phases resulting from step (f);
(h) vacuum drying the organic phase resulting from step (g) to remove pentane and other volatiles at an elevated temperature; and
(i) filtering the organic phase resulting from step (h) to obtain a treated di-t-nonyl polysulfide.

16. A process according to claim 15 wherein said crude di-t-nonyl polysulfide is prepared by:
(j) contacting stoichiometric amounts of elemental sulfur with t-nonyl mercaptans in the presence of triethylene catalyst to form a crude product with an average of about 5 sulfur atoms per polysulfide molecule and to form gaseous hydrogen sulfide; and
(k) removing residual hydrogen sulfide form said crude product.

17. A process according to claim 16 wherein said residual hydrogen sulfide is removed by an inert gas purge.

18. A process according to claim 16 wherein said residual hydrogen sulfide is removed by vacuum stripping.

19. A process according to claim 16 wherein said residual hydrogen sulfide is removed by heating.

20. A process for treating a crude polysulfide comprising the steps of:
a) contacting said crude polysulfide with a high pH aqueous phase to produce a polysulfide-contacted high pH aqueous phase and a high pH treated polysulfide-bearing organic phase; and
b) separating said polysulfide-contacted high pH aqueous phase and said high pH treated polysulfide-bearing organic phase, and further comprising the following steps which are performed after the steps (a) and (b):
(c) contacting high pH treated polysulfide-bearing organic phase with a low pH aqueous phase to give a polysulfide-bearing organic phase; and
(d) separating said polysulfide-contained low pH aqueous phase and said low pH treated polysulfide-bearing organic phase.

21. A process according to claim 20 wherein said crude polysulfide is obtained by contacting elemental sulfur with alkyl mercaptans containing 3 to 20 carbons in the presence of a basic catalyst.

* * * * *